United States Patent [19] Pelton

[11] 4,366,721

[45] Jan. 4, 1983

[54] MOLTEN METAL SAMPLING DEVICE

[75] Inventor: John F. Pelton, Yorktown Heights, N.Y.

[73] Assignee: Union Carbide Corporation, Danbury, Conn.

[21] Appl. No.: 233,110

[22] Filed: Feb. 10, 1981

[51] Int. Cl.$^3$ .............................................. G01N 1/12
[52] U.S. Cl. ............................... 73/863.23; 73/864.55
[58] Field of Search ........... 73/863.23, 863.25, 864.53, 73/864.54, 864.55

[56] References Cited

U.S. PATENT DOCUMENTS 3,820,380 6/1974 Miller .............................. 73/864.55
4,179,931 12/1979 Moriya ............................ 73/864.54
4,291,585 9/1981 Kolb ................................ 73/863.23

*Primary Examiner*—S. Clement Swisher
*Attorney, Agent, or Firm*—Saul R. Bresch

[57] ABSTRACT

In a molten metal sampling device having a porous filter connected by a conduit to a reservoir in such a manner that molten metal can be drawn, by vacuum, down into the filter and then to the reservoir, a removable seat for the filter, a stopper rod to prevent the flow of metal until the optimum moment, and an insulated, inert lining for the unsubmerged parts, which is permeable to generated gases, are provided.

7 Claims, 2 Drawing Figures

1 2 2 2 3 4 5 6 7 8 7 9 10 14 17 12 13 18 16 15 11

MOLTEN METAL SAMPLING DEVICE

FIELD OF THE INVENTION

This invention relates to a molten metal sampling device.

DESCRIPTION OF THE PRIOR ART

Sampling of molten metal for analytical purposes is common in industrial refining where the quality of the metal is important in its ultimate application, e.g., the use of aluminum in the fuselage of aircraft. Molten aluminum is refined by various methods including sparging as in U.S. Pat. No. 3,870,511, settling, or filtration. The purpose of these refining techniques is the removal of dissolved hydrogen, alkali metals, and/or solid non-metallic particles, usually metal oxides. The degree of contamination at any point in the refining process can be easily determined with respect to dissolved hydrogen or alkali metals by simply taking a liquid sample with a ladle or its equivalent, pouring the molten aluminum into a mold and subjecting the solidified sample to standard chemical analysis. This procedure is not effective for solid non-metallic particles (known as inclusions), however. One problem is that the sampling procedure itself is liable to introduce more inclusions. The other problem is that the inclusions that cause quality problems in the aluminum are often quite small and widely dispersed in the melt. This makes the inclusions difficult to locate by standard metallographic methods. In addition, the size and shape of the oxide inclusions are as important as the total amount present, and size and shape cannot be determined by chemical analysis.

An approach that has been used to determine solid inclusion content is to pass a sample of liquid metal through a filter. This concentrates the particles on the surface of the filter where they can be observed using standard metallographic techniques. If the sample is removed from the melt by ladling, the sampling procedure itself, as noted above, may contaminate the sample. An alternate approach is to introduce the filter directly into the melt to avoid the contamination caused by intermediate handling. This is accomplished by inserting the filter in a holding device, immersing the device in the melt and drawing the molten metal through the filter by vacuum. In order to prevent the liquid metal from running away from the filter, the liquid is drawn through the filter in a downward direction. This, of course, prevents loss of collected particles.

The sampling technique was further improved by the use of fine filters made of carbon or graphite; the plugging of the entrance to the filter to provide an opportunity for preheating the filter and the filter holder; and the solidification of the metal sample from the bottom to the top to avoid shrinkage voids in the filter area.

While each of the foregoing improved on the basic sampling device, those involved with the aluminum industry have continued to seek a further optimization.

SUMMARY OF THE INVENTION

An object of the invention, therefore, is to provide an improvement in previously known molten metal sampling devices whereby the resultant sample is as representative as possible of the metal being tested; the metal is not changed in inclusion content by the manner in which the device must be used; the device is simple and practical, i.e., the sample is easily removable; unwanted freeze-ups are avoided; and the device for the most part can be reused.

Other objects and advantages will become apparent hereinafter.

According to the present invention, such an improvement has been discovered in a molten metal sampling device comprising the following components in combination:

(i) a porous filter;

(ii) holding means for said filter;

(iii) a hollow conduit running from a point adjacent to and below the filter through the holding means to a covered reservoir; and (iv) vacuum means connected to the reservoir through an aperture in the cover, the components being positioned in such a manner that molten metal can be drawn through the filter in a downward direction and, then, through the conduit into the reservoir.

The improvement comprises:

(a) providing a recess in the holding means;

(b) in the upper portion of the recess providing a hollow cup, snugly fitted, but removable; open at both ends; and with a peripheral seat intermediate of both ends on which the filter resides;

(c) providing a removable stopper rod, which fits into that portion of the cup above the filter; and (d) providing a contiguous lining for that part of the conduit, which will not be submerged in the molten metal, and for the reservoir and its cover, said lining comprising an insulating material inert and essentially impervious to molten metal, but permitting the passage of gases therethrough.

DESCRIPTION OF THE PREFERRED EMBODIMENT

Figures 1, 2:
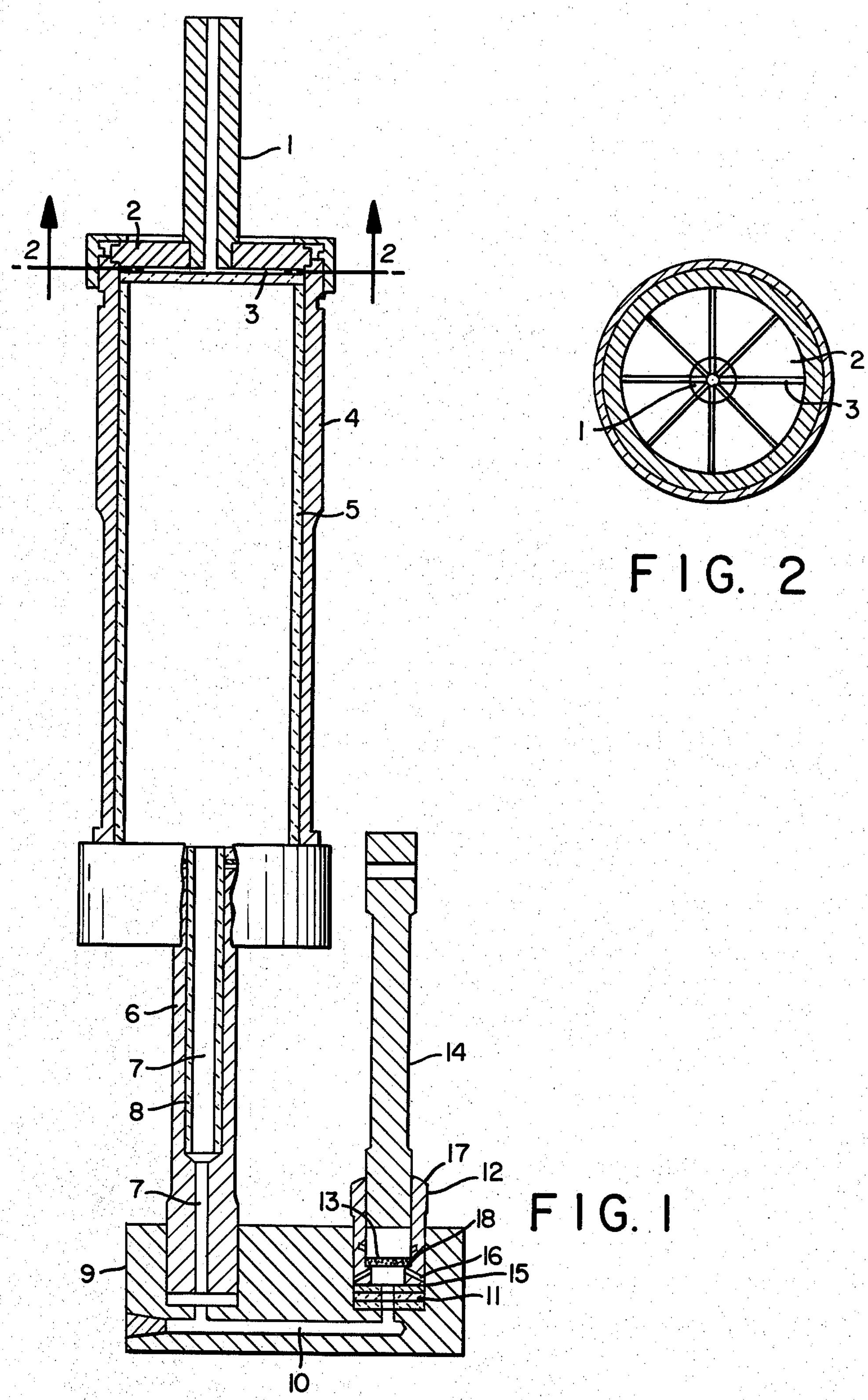
FIG. 1 is a schematic diagram of a cross-section of an embodiment of the invention.
FIG. 2 is a schematic diagram of a bottom view of a cross-section taken at line 2—2 of FIG. 1.

The molten metal sampling device comprises vacuum pump means (not shown), vacuum pipe 1, reservoir cover 2 containing radial grooves 3, reservoir 4 containing insulation 5, stem 6 with conduit 7 and insulation 8, filter holder 9 with conduit 10, plugs 11, filter cup 12, filter 13, and stopper rod 14. Vacuum pipe 1, reservoir 4, conduits 7 and 10, and filter cup 12 are, of course, connected to each other through various apertures. After a vacuum is applied to the system with stopper rod 14 in place, the device is lowered into the molten metal to be sampled until the device is immersed to a point above the beginning of insulation 8, i.e., above the lowest point reached by the insulation in stem 6, the vertical axes of both stem 6 and stopper rod 14 being about perpendicular to the surface of the melt. The device is immersed to a point above the beginning of the insulation, as much as half way up insulator 8, in order to avoid having the aluminum freeze before it reaches the reservoir and also to bring conduits 7 and 10 up to a sufficient temperature to melt the residual aluminum from the previous sample. After the submerged portion of the device is preheated to melt temperature, stopper rod 14 is removed. The liquid metal is then drawn down through filter 13, through conduits 10 and 7, and into reservoir 4. As the molten metal passes through filter 13, some of the solid inclusions (depending on size and degree of agglomeration) are retained on and in the filter. When reservoir 4 is full, the device is removed from the melt, the liquid metal in the device is allowed to cool and solidify, and then the vacuum pump is shut off.

It is advantageous, on removal of the device, to apply a conventional chilling device, e.g., a closely fitting graphite block or air jet, to filter holder 9 at a point below filter 13 to promote directional solidification of the liquid metal from the bottom to top. This allows the free liquid in the zone above filter 13 to feed the shrinkage, thus avoiding shrinkage holes in that zone. When the device is cool, filter cup 12, together with filter 13 and solidified metal above and below filter 13, are removed from filter holder 9 and sectioned and evaluated by standard metallurgical techniques, and the particles on and in the filter can be measured, counted, analyzed, and photographed.

Filter 13 is cemented at peripheral seat 18 into tapered filter cup 12, which is open at both ends. This provides a sub-assembly which can be installed in the device and then removed with the desired sample after the sampling procedure is completed. To this end, filter holder 9 is provided with a tapered socket 15 or recess which will receive filter cup 12. Filter cup 12 is designed internally to anchor in place metal slugs above and below filter 13 so that they are not separated from filter 13 during solidification or subsequent handling, such separation making evaluation very difficult. It will be observed that filter 13 rests upon seat 18 (or a step) in the wall of filter cup 12. Anchor holes 16 are provided above and below filter 13. These anchor holes 16 comprise a number of holes (typically four) drilled into the wall of filter cup 12. The holes may be drilled through below filter 13, but, above filter 13, such through drilled holes are undesirable because they would invite contamination of the surface of filter 13 from the outside.

It is found that even with anchor holes 16, shrinkage of the slug of metal above filter 13 causes it to pull away from the filter (or pull filter 13 away from the metal below) if the metal is anchored at the top (or lip) of the filter cup by permitting the metal to extend out over the lip. This undesirable effect is eliminated by shaping lip 17 of filter cup 12 as shown, i.e., providing a top bevel and a corner radius such that most of the liquid metal is caused to run off lip 17 away from filter cup 12 when the device is withdrawn from the melt. Typical bevels that can be used are 20 to 30 degrees down from the horizontal and typical corner radii are 1/16 to ⅛ inch.

Filter cup 12 and socket 15 are sized so that when the filter cup is pushed and twisted by hand into the socket, a sufficiently good seal is made without the need for any cement. After use, filter cup 12 can be removed by first twisting it to break the metal connection between the filter cup and filter holder 9. This removal, as well as the re-installation of a new filter cup, is facilitated by filling up essentially all of the space in socket 15 underneath filter cup 12 with plugs 11 made, for example, of ceramic fiber insulating paper or blanket. The plugs, of course, are perforated in the center to permit the free flow of molten metal. A hollow cylinder open at both ends or washers can be substituted for plugs 11 and, in the context of this specification, plugs are defined to include these and other equivalents. It will be understood that the plugs should be made of a material which will not melt or decompose when exposed to the molten metal and will not be capable of penetration by the liquid metal under operating conditions. Further, the plugs are preferably made of a material, which is compressible, and, taken together, slightly larger than the space, which they are to fill. Thus, the melt is substantially excluded from the space except for the central hole area, i.e., the perforations mentioned above. The perforations or central hole are made just large enough to provide for unobstructed flow of metal during the sampling procedure. This leaves a metal core, which can be easily broken during cup removal and later cut away.

A desirable filter material for use in molten metal environments is porous graphite. Graphite, however, is not readily wetted by liquid metals. Therefore, sufficient pressure is needed to overcome the surface tension of the liquid metal and cause it to penetrate the filter pores, and the smaller the pores, the greater the pressure required for adequate penetration. Since the procedure used for collecting samples is best carried out at atmospheric pressure, only one atmosphere of pressure is available to drive the liquid metal through the pores of the filter. This procedure, then, sets a lower limit on the fineness of the filter pores, which can be used in the device. Taking this lower limit into consideration, the filters with the finest, i.e., smallest pores, are used in order to retain the smallest possible inclusion particles. The filters would be of that fineness compatible with the capability of having liquid metal driven through the pores by one atmosphere of pressure. To facilitate a rapid, uniform, and consistent start for the liquid flow, stopper rod 14 is removed while full vacuum, i.e., the highest vacuum the pump is capable of, is being applied. The in-rush of liquid, with some impact on the filter surface, facilitates the start. In order that this can be accomplished, the diameter of stopper rod 14 is preferably such that the withdrawal force required to remove the rod from filter cup 12 does not make hand manipulation too difficult. Typical filter pore sizes are in the range of about 30 to about 60 microns; stopper rod diameters are in the range of about ⅜ to about ½ inch; and filter cup diameters at the top of the cup are in the range of about ¾ to about 1 inch. With the exception of filter 13, plugs 11, and insulation 5 and 8, the device can be made of the following materials: the portion that comes in contact with the metal bath should be resistant to attack by the liquid metal; when the metal is aluminum, graphite is a convenient material. Ceramic materials can also be used. The reservoir and other out-of-melt parts can be steel, preferably stainless steel for long life.

The filter and other portions of the device, which are submerged in the liquid metal during the sampling procedure, are preheated to melt temperature before stopper rod 14 is removed and are, of course, kept at melt temperature while the sample is being taken. Other portions of the device, e.g., reservoir 4 and part of stem 6, which are not submerged would be quickly clogged up with solidified metal because of their low temperature. In order to avoid this initial freeze-up without applying external heat, these portions of the device are insulated on the inside with an insulating material which cannot be penetrated by the molten metal such as a ceramic fiber paper, e.g. Fiberfrax ceramic fiber paper number 970-J made by The Carborundum Company and having a normal thickness (uncompressed) of ⅛ inch. Another conventional insulating material, which can be used, is Kaowool ceramic fiber paper manufactured by Babcock & Wilcox Company.

It will be noted that conduit 7 has a large diameter in its upper portion, which is insulated, and a narrow diameter in its lower portion which is not, and that insulation 8 covers both the submerged and unsubmerged part of the upper portion of conduit 7. The reason why the device is submerged to an intermediate point on insulation 8 was explained above. The reason for the step down in the diameter of conduit 7 is to facilitate breakage. After solidification, the core of metal in the insulated portion of stem 6 can be twisted and pulled out with the break occurring at the beginning of or within the narrow, uninsulated portion of the stem. This cleans out all of the metal from the part of the stem that will not be melted out during the next insertion of the device in molten metal thus allowing re-use of the part.

When the metal withdrawal is completed and the device is removed from the melt, the metal in the filter cup solidifies preferably in a direction from the bottom of the filter cup to the top of the filter cup. During the transition from liquid to solid, it is desirable to have little, if any, flow down through the filter and no flow in the reverse direction. Too much flow down through the filter may leave no metal on top of the filter, making evaluation difficult. Any reverse flow will lift the layer of filtered-out solids off of the filter surface, again making evaluation difficult or impossible.

The control of the flow during the transition period is accomplished by the design of reservoir cover 2. It has been noted that reservoir 4 is lined with insulation 5, the same kind of insulation as that used in stem 6. The insulation used is preferably sufficiently porous so that the gas in the device will flow to vacuum pipe 1 with very little restriction. To make sure that any restriction of gas is kept at a minimum, reservoir cover 2 has on its lower surface a number of radial grooves 3 communicating with an aperture in the center of cover 2 which opens into vacuum pipe 1. Beneath cover 2, insulation 5 is present, typically in the form of a disc where the reservoir is cylindrical. There is no aperture in this insulation. When the rising molten metal reaches this insulation beneath cover 2, the flow is essentially stopped because the liquid cannot penetrate the insulation. Some metal may pass through the joint between the cover insulation and the side-wall insulation, however. This metal will be drawn toward the central aperture in cover 1 via radial grooves 3, but will solidify by contact with relatively cold cover 2 before reaching and plugging the aperture. It is noted that cover 2 is a part of reservoir 4 and that the entire reservoir 4 including, of course, cover 2 is lined with insulation 5 except at the aperture where conduit 7 feeds into reservoir 4. While the insulation lined with insulation 5 except at the aperture where conduit 7 feeds into reservoir 4. While the insulation is contiguous, however, it is, generally, not in one piece.

The fibers of ceramic fiber paper and other insulating materials are bonded together with an organic material to facilitate handling. This organic material is vaporized or pyrolized by the heat from the molten metal, the resulting gases being driven out through the aperture in cover 2 and vacuum pipe 1. This gas generation may continue for some time after reservoir 4 has been filled with molten metal. The device is constructed in such a manner that these gases are freely vented and are not allowed to build up any pressure within the reservoir since the pressure would force liquid metal out of the reservoir and back up through the filter. Free venting may be accomplished by assembling the pads (or blankets) used for insulation so that each pad touches the one next to it. The contiguous insulation 5 together with radial grooves 3 form a continuous channel for gas flow from any portion of the insulation to the aperture in cover 3, even when the device is completely full of metal.

The sampling device is typically supported by a main frame which provides means for supporting the device; raising and lowering the device into the melt; and for continually weighing the device during the sampling procedure. This frame is of conventional construction and will not be described here except with regard to the weighing means, which is considered to be quite advantageous to the sampling procedure.

The device, of course, increases in weight as it is filled with metal. By monitoring its increase in weight during sampling, a clear picture is obtained of the flow through the filter from start to finish, one which could not be obtained visually because of the opacity of the melt. Thus, it is readily ascertained that the flow through the filter did or did not start when the stopper rod was removed from the filter cup. One can also tell when the reservoir 4 is full or that the flow into reservoir 4 stopped at some point before it was filled. By timing the weight change during the sampling a picture is obtained of the flow rate through the filter at all times during the sampling procedure.

The weighing is preferably accomplished by fastening the device to a mounting block, which is, in turn, fastened to the main frame through a set of leaf springs. Motion of the chamber mounting block relative to the main frame is measured by a dial indicator. This motion, in conjunction with the known spring constant, can be used to calculate weight changes. While this is a convenient mechanical arrangement, the weighing can also be done by other means, such as by load cells of various types. An important part of the weighing process is the proper handling of stopper rod 14. It is hung on the mounting block, after it is removed from the filter cup, in about the same vertical position that it was in before its removal so as to maintain the same degree of immersion in the liquid metal. In this manner, the total weight sensed by the weighing device is not influenced by the removal of stopper rod 14 and the previously set starting point in the weighing process is preserved.

I claim:

1. In a molten metal sampling device comprising the following components in combination:

(i) a porous filter;

(ii) holding means for said filter;

(iii) a hollow conduit running from a point adjacent to and below the filter through the holding means to a covered reservoir; and (iv) vacuum means connected to the reservoir through an aperture in the cover, the components being positioned in such a manner that molten metal can be drawn through the filter in a downward direction and, then, through the conduit into the reservoir, the improvement comprising:

(a) a recess in the holding means;

(b) in the upper portion of the recess, a hollow cup, snugly fitted, but removable; open at both ends; and with a peripheral seat intermediate of both ends on which the filter resides;

(c) a removable stopper rod, which fits into that portion of the cup above the filter, and (d) a contiguous lining for that part of the conduit, which will not be submerged in the molten metal, and for the reservoir and its cover, said lining comprising an insulating material inert and essentially impervious to molten metal, but permitting the passage of gases therethrough.

2. The device defined in claim 1 wherein the filter is made of graphite.

3. The device defined in claim 1 wherein anchor holes are drilled into the wall of the cup, above and below the filter.

4. The device defined in claim 1 wherein the upper end of the cup has a beveled lip and a rounded outer edge, the angle of the bevel and the radius of the edge being such that when the cup is in a vertical position, gravity will cause molten metal to flow over the lip away from the cup.

5. The device defined in claim 1 wherein the lower portion of the recess is essentially filled with at least one hollow plug open at both ends, said plug comprising a material inert and essentially impervious to molten metal.

6. The device defined in claim 5 wherein the part of the conduit which is not to be submerged has a larger diameter than the lower portion of the part of the conduit which is to be submerged, and the lining covers the part of the conduit, which has the larger diameter.

7. The device defined in claim 1 wherein the cover has at least one radial groove on the reservoir side, said radial groove running from the periphery of the cover to the aperture.

* * * * *